United States Patent [19]

Riebschleger

[11] Patent Number: 5,435,720
[45] Date of Patent: Jul. 25, 1995

[54] RETENTIVE ORTHODONTIC DENTAL BRACKET

[76] Inventor: Ronald P. Riebschleger, 12840 Edgerton NE., Cedar Springs, Mich. 49319

[21] Appl. No.: 182,431

[22] Filed: Jan. 18, 1994

[51] Int. Cl.$^6$ ............................................. A61C 3/00
[52] U.S. Cl. ................................................... 433/9
[58] Field of Search ................................... 433/8, 9

[56] References Cited

U.S. PATENT DOCUMENTS

| | | | |
|---|---|---|---|
| 3,765,091 | 10/1973 | Northcutt | 433/9 |
| 3,932,940 | 1/1976 | Andren | 433/9 |
| 4,063,360 | 12/1977 | Waller | 433/9 |
| 4,094,068 | 6/1978 | Shinhammer | 433/9 |
| 4,100,678 | 7/1978 | Yatabe | 433/9 |
| 4,165,561 | 8/1979 | Miller et al. | 433/9 |
| 4,604,057 | 8/1986 | Viglietti | 433/9 |
| 4,735,569 | 4/1988 | Munk | 433/9 |
| 4,773,857 | 9/1988 | Herrin | 433/9 |
| 5,263,859 | 11/1993 | Kesling | 433/9 |

Primary Examiner—Cary E. O'Connor
Attorney, Agent, or Firm—Waters & Morse

[57] ABSTRACT

An improved orthodontic dental bracket with glue openings in the form of notches in the edges of the base plate or apertures in the interior of the base plate of the bracket. The openings can have outwardly diverging side walls. During application of the bracket the glue openings serve to direct dental adhesive to flow into the openings and induce the adhesive to form an enlarged head toward the outer surface of the bracket's base plate. Once the glue has cured, the column of glue and enlarged head provides a positive mechanical lock to further secure the dental bracket to the glue layer.

9 Claims, 2 Drawing Sheets

RETENTIVE ORTHODONTIC DENTAL BRACKET

BACKGROUND OF THE INVENTION

This invention relates to an improved orthodontic dental bracket, commonly known as braces, to assist in the straightening or repositioning of teeth in the mouth of a patient. More particularly, this invention relates to the addition of notches or apertures in the base plate of the dental bracket which permit dental adhesive to flow into the bracket and form a mechanical lock between the adhesive and the dental bracket.

Orthodontic dental brackets have been in use for many years in the field of dentistry to aid in the correction of misaligned teeth. The dental brackets may be made of metal, porcelain, plastic, or glass and are affixed to the teeth by cleaning the tooth and gluing the bracket to the tooth with a dental adhesive. Dental wire is then threaded from dental bracket to dental bracket and tensioned appropriately. The tensioning of the dental wire provides lateral forces on the tooth via the dental bracket so that over a period of time a patient's teeth are gradually coerced into a desired alignment.

Critical to the successful completion of this process is the requirement that a strong and unbreakable glue bond be formed between the dental bracket and the tooth.

The typical process in bonding a dental bracket to a tooth involves a series of steps substantially as described below.

1. The tooth to which the bracket is to be applied is polished with pumice with a rubber cup polisher to remove debris and to establish clean enamel.
2. The tooth is "conditioned" or etched for 20–60 seconds. The etching is accomplished using an acid-like substance such as phosphoric acid. The etching process removes a smear layer and leaves enamel "tags," or the rods and tubules remaining after etching. The rods and tubules provide some mechanical retention between the glue layer and the tooth.
3. A bonding agent is placed onto the tooth for better retention between the enamel and the glue. The bonding agent is usually an unfilled resin which is either light-cured or self-cured.
4. A dental adhesive is placed on the dental bracket's tooth side surface. This surface usually includes a surface pattern in different directions to provide a "meshwork" pattern. The dental adhesive applied to the tooth is typically either a filled resin, unfilled resin, or various forms of composite resins or glues and is "buttered" onto the meshwork surface of the bracket. For convenience herein, unless the term glue is being used to distinguish one type of dental adhesive from a dental adhesive formed of a different material, the terms dental adhesive and glue will be used synonymously to refer to any dental adhesive. There is a weak mechanical and weak chemical bond between the glue and the bracket meshwork. At this critical point nothing may touch the bracket. Some brackets are pre-glued to speed the process and decrease the chance of contamination.
5. The glued dental bracket is then placed on the tooth and the glue is allowed to cure by itself or cured under a blue light.

In order for the dental bracket to perform its desired function there must be a strong glue-tooth bond and a strong glue-bracket bond. Failure of the glue-tooth bond is rarely experienced; however, the bond between the dental bracket and the glue is found to fail quite often. When the bond fails, the tooth alignment process is interrupted and the bracket must be reattached or a new bracket attached to the tooth. This requires the patient to revisit the orthodontist at an extra unscheduled office visit.

Providing a stronger bond between the dental bracket and the glue will prevent the brackets from separating from the tooth and correspondingly reduce unnecessary visits to the orthodontist. The stronger bond also makes it possible to apply more force to the tooth through the bracket for the orthodontic treatment. Therefore, the purpose of the present invention is to improve the bond between the glue layer and the dental bracket by improving the glue-bracket mechanical bond.

SUMMARY OF THE INVENTION

The improved orthodontic dental bracket according to the present invention utilizes one or more glue retaining openings in an orthodontic dental bracket base plate, with the openings being formed as notches in the periphery of the base plate or one or more internal apertures or holes in the base plate. Multiple openings enhance the mechanical retention and restrain rotation of the bracket.

The orthodontic dental bracket is bonded or glued to a patient's tooth with a dental adhesive such as a resin or glue. When a conventional dental bracket is applied to the tooth, excess adhesive emanates from the periphery of the base plate and flows in a direction laterally from the base plate. The openings added to the base plate in the present invention have opposing sides which direct some of the excess adhesive up through the openings along the sides thereof. The adhesive can then be flattened out over the outer surface of the base plate in order to form an enlarged head on the glue column that resists outward dislodgment of the dental bracket. Alternatively or in addition, the sides of the opening can be inclined so as to diverge in an upward and outward direction. The diverging sides produce an enlarged head or outer portion on the glue column that resists outward displacement of the dental bracket away from the tooth. When the adhesive cures, the column of adhesive and enlarged head provide a positive mechanical lock of the bracket to the adhesive and improves on the normally weak glue-bracket chemical bond.

One embodiment of the present invention utilizes openings in the form of U-shaped notches on opposite sides of the base plate. The mechanical bond is further enhanced if the distance across the mouth of the U-shaped notch is narrower than the distance across the notch inwardly from the mouth toward the center of the bracket. The narrower mouth dimension prevents the dental bracket from slidably disengaging from the glue column in a lateral direction through the mouth, thereby more firmly retaining the bracket on the glue layer. The sides of the notch can be parallel or outwardly diverging at the outer side of the bracket.

Another embodiment of the invention utilizes an inverted frustal aperture or hole in the base plate for forming the glue column. The aperture or hole functions in a manner similar to the notch by directing excess glue toward the outer surface of the base plate. The aperture's smaller diameter at the inner base plate surface than at the outer surface provides the locking feature of the enlarged head on the glue column. The advantage of this embodiment is that the aperture may be located anywhere within the base plate periphery, even under the attached dental wire bracket, thus adding to the aesthetics of the dental bracket. The aperture can extend partially through the base plate or all of the way through the base plate.

These and other features of the present invention are described and shown in more detail below in connection with a description of the preferred embodiments of the present invention.

DESCRIPTION OF THE PREFERRED EMBODIMENTS

Figure 1:
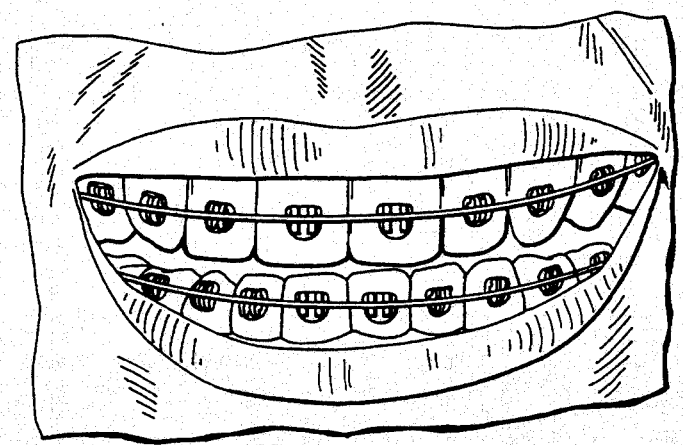
FIG. 1 is a frontal view of a person having a plurality of braces in actual use.
Figure 2:
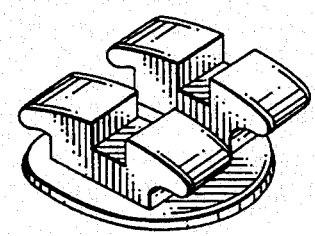
FIG. 2 is an isometric view of a typical prior art orthodontic dental bracket in current use.
Figure 4:
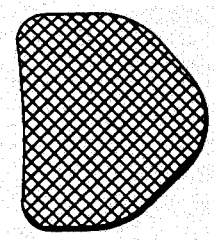
FIG. 4 shows the inner side of a prior art piece of dental hardware illustrating a conventional mesh configuration.
Figure 5:
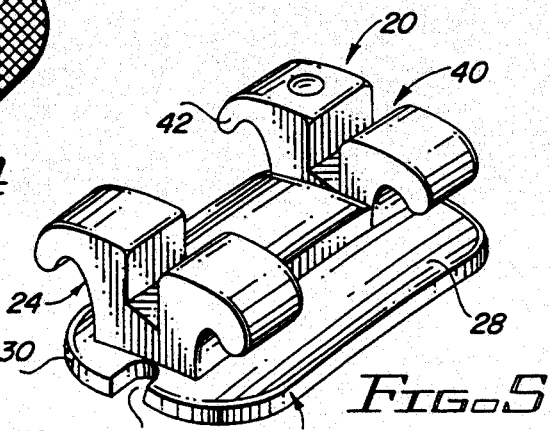
FIG. 5 is an isometric view of the improved dental bracket showing the added glue notch in the base plate, with the sides of the notch being parallel and perpendicular to the base.
Figure 3:
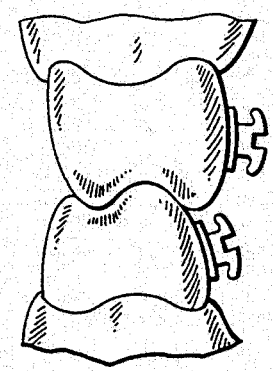
FIG. 3 is a side view showing the manner in which prior art orthodontic dental hardware is attached to the teeth.
Figure 6:
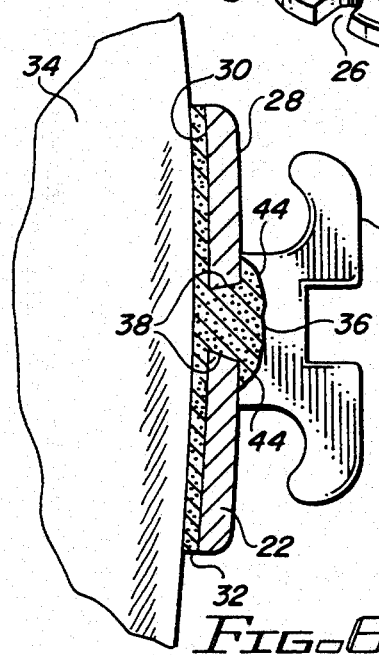
FIG. 6 is an enlarged and slightly modified sectional side view of FIG. 5 showing the notches with outwardly diverging opposed side walls and showing the glue spread laterally over the outer surface of the base plate and forming the mechanical finger.
Figure 7:
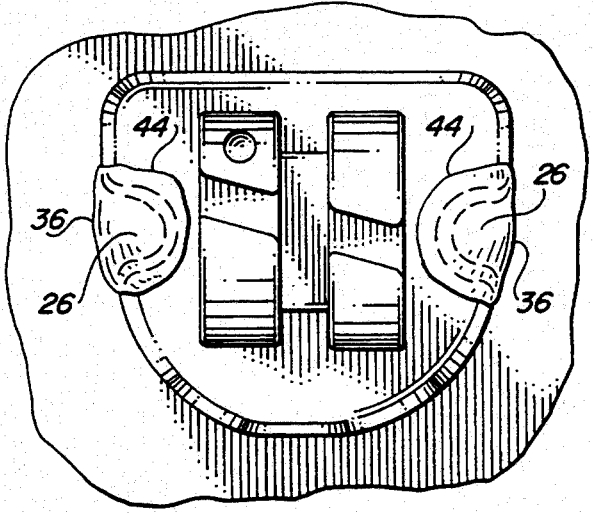
FIG. 7 is a top view of the dental hardware of FIG. 6.

Referring to the drawings and more particularly to FIGS. 5-7, an improved orthodontic dental bracket 20 is provided in accordance with the present invention. The dental bracket 20 has a wire bracket 24 permanently affixed to a base plate 22. The wire bracket comprises slots 40 and tabs 42 for receiving dental wire and rubber bands or wire ligatures to retain the dental wire respectively. The base plate 22 is essentially flat or slightly curved to match the contour of a tooth 34. The base plate 22 has an inner side 30 which is placed against the tooth 34 and an outer side 28 to which the wire bracket 24 is affixed. The base plate 22 extends a sufficient distance beyond the wire bracket 24 to permit the formation of notches 26 in opposing ends of the base plate 22. Notches 26 are essentially U-shaped in configuration and extend from the inner surface 30 to the outer surface 28. Each notch has opposing sides 38 to guide the flow of glue 32 from the inner surface 30 toward the outer surface 28. The sides can be parallel and perpendicular to the base, as shown in FIG. 5, but the sides 38 preferably are outwardly diverging or chamfered, as shown in FIGS. 6 and 7.

During the application of the dental bracket 20 to the tooth 34, a layer of glue 32 is first applied to the inner surface 30 of the base plate 22. A gentle force toward the tooth is then applied to the dental bracket 20 causing excess glue to flow out from the periphery of the base plate 22. The flow of the glue 30 is generally unrestricted and flows away from the periphery of base plate 22. However, the opposing sides 38 of notches 26 serve to direct the flow of glue 32 through the notch 26 toward the outer surface 28. Once the flow of glue protrudes from the outer surface 28, it is flattened out in mushroom fashion to form an enlarged head 36 around notch 26 and over the outer surface 28. The overflow of glue forms a locking finger of glue 44 over the periphery of notch 26, providing a positive mechanical locking feature between the base plate 22 and the glue 30. The diverging sides serve the same purpose by providing an enlarged wedge shaped portion of glue adjacent the outer surface that cannot be pulled inwardly through the notch to pull the base plate away from the tooth.

Notches 26 are provided on each of opposing ends of the base plate 22 to prevent the dental bracket 20 from slidably disengaging from the formed glue layer 32 and the glue mushroom or head 36. The ends chosen for inclusion of the notches 26 are not critical to the described invention, but it is desired that the notches 26 are essentially on opposite sides from each other.

Figure 8:
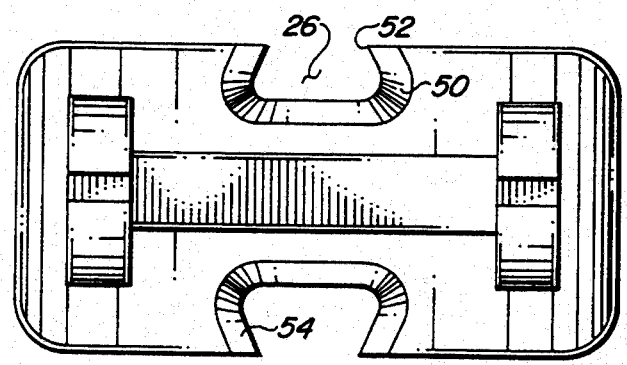
FIG. 8 is a top view of a piece of dental hardware showing an alternate embodiment of the invention.
Figure 9:
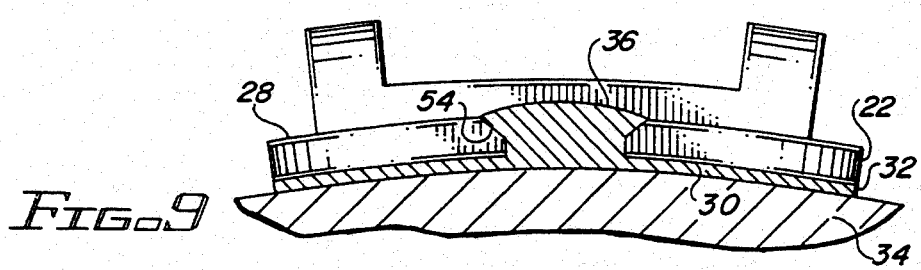
FIG. 9 is a side view of FIG. 8 showing the chamfered edges of the glue notch on the outer surface of the base plate.

An alternate embodiment of the present invention is shown in FIGS. 8-9. In this embodiment the U-shaped notch 26 is modified such that the closed portion 50 of the "U" is slightly larger than the open portion 52 of the "U". This configuration aids in the prevention of slidable disengagement of the bracket 20 from the glue layer 32 since the mushroom column 36 is of a greater dimension than the width of the open portion 52 of the "U". Another feature shown in this embodiment is the addition of a chamfer 54 around the periphery of the notch 26 that widens as it extends outwardly toward outer surface 28. The chamfer 54 aids in promoting the mushroom-like expansion of the glue column 36 as it is directed through the notch 26. The chamfer 54 results in a lower profile mushroom and improves the aesthetic appearance of the attached dental bracket 20.

Figure 10:
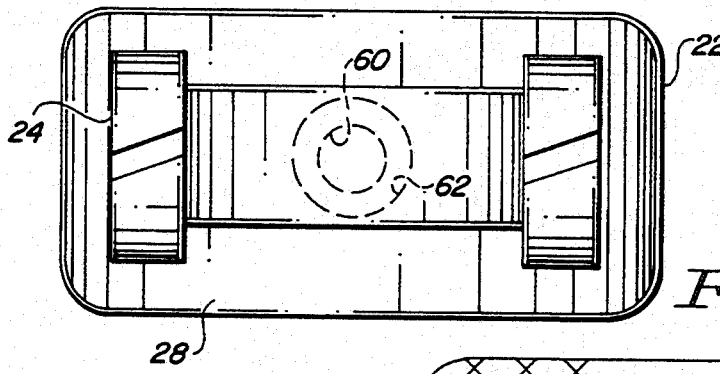
FIG. 10 is a top view of a third embodiment of the invention showing a glue aperture in the base plate under the dental wire bracket.
Figure 11:
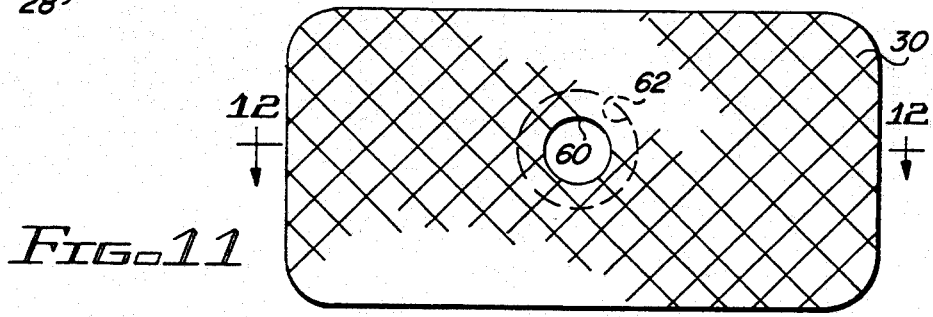
FIG. 11 is a bottom view of FIG. 11.
Figure 12:
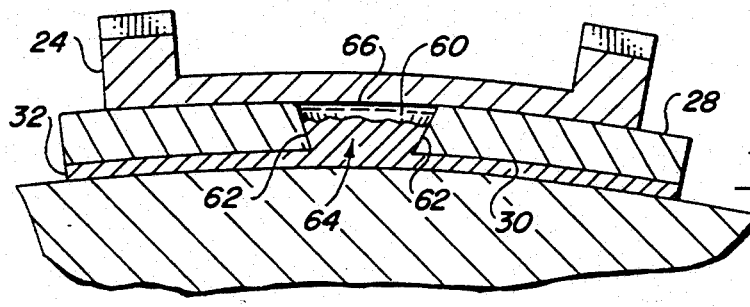
FIG. 12 is a sectional view of FIG. 11 showing the inverted conical glue aperture.

A third embodiment is disclosed in FIGS. 10-12. This embodiment shows one aperture 60 through the base plate 22 (although more than one aperture may be used). The configuration of the aperture 60 is that of an inverted frustum such that its diameter 64 at the inner surface 30 is smaller than its diameter 66 at the outer surface 28. The aperture 60 also has opposing sides 62 which serve to direct the flow of glue 32 up through the aperture 60. When the glue 32 cures the inverted frustal shape acts in a fashion similar to the mushroom column 36 described in the previous embodiments. Additionally, since the aperture does not open to the periphery of the base plate, even a single aperture will prevent the dental bracket 20 from slidably disengaging from the glue layer. The aperture 60 may be hidden under the wire bracket to improve the aesthetic aspect of the dental bracket 20.

The foregoing is representative of the preferred practice of the present invention. Various changes may be made in the embodiments disclosed herein without departing from the spirit and scope of the present invention, as defined in the appended claims.

I claim:

1. In an orthodontic dental bracket comprising a base plate having an inner side that is adapted to be attached to a tooth surface by a dental adhesive and an outer side on which a dental wire bracket is positioned, the improvement wherein the base plate comprises a notch formed in an edge of the base plate that extends laterally inwardly into the base plate from an open mouth at the edge of the base plate, the notch having opposed sides extending into the base plate on each side of the mouth, the notch being shaped such that dental adhesive flows into the opening when the base plate is pressed against dental adhesive positioned on a tooth surface, the portion of the dental adhesive that flows into the opening providing mechanical resistance to perpendicular and lateral displacement of the base plate from the tooth surface.

2. A dental bracket according to claim 1 and further comprising a second notch formed in the periphery of the base plate on a generally opposite side of the base plate from the other notch.

3. A dental bracket according to claim 1 wherein the notch is generally U-shaped, with legs of the "U" comprising the sides of the notch and an open side of the "U" facing laterally outwardly from the outer edge of the base plate comprising the mouth of the notch.

4. A dental bracket according to claim 3 wherein the distance across the sides at the mouth of the U-shaped notch is less than the distance between the sides of the notch laterally inwardly from the mouth, such that sides of the notch at the mouth resist lateral displacement of the dental adhesive outwardly from the notch through the mouth.

5. A dental bracket according to claim 1 wherein at least the opposed sides of the notch diverge outwardly as the notch extends from the inner to the outer side of the base plate, the adhesive filling the space between the diverging sides forming an enlarged head on the adhesive in the notch.

6. A dental bracket according to claim 1 and further comprising a second notch formed in the peripheral edge of the base plate at a position spaced apart from the first notch.

7. In an orthodontic dental bracket comprising a relatively flat base plate having an inner side that is adapted to be mounted on a tooth surface and having a dental wire bracket mounted on an outer side thereof, the improvement wherein:

the base plate includes opposed U-shaped notches in outer edges of the base plate, with the notches being formed such that dental adhesive positioned between the base plate and a tooth flows into the notches when the base plate is pressed against the adhesive, the adhesive then forming a mechanical lock to hold the base plate securely on the tooth.

8. An orthodontic dental bracket as described in claim 7 wherein the distance across an open mouth of at least one of the U-shaped notches at the edge of the base plate is smaller than the distance across a portion of the U-shaped notch inward from the edge, such that the adhesive in the notch is restrained from slidably disengaging from the base plate outwardly through the open mouth of the notch.

9. An orthodontic dental bracket as described in claim 7 wherein the U-shaped notches are shaped to make the notches of greater cross-sectional area on the outer surface of the base plate than on the inner surface.

* * * * *